United States Patent [19]

Sioshansi et al.

[11] Patent Number: 5,123,924
[45] Date of Patent: Jun. 23, 1992

[54] SURGICAL IMPLANTS AND METHOD

[75] Inventors: Piran Sioshansi, Lincoln; Eric J. Tobin, Burlington, both of Mass.

[73] Assignee: Spire Corporation, Bedford, Mass.

[21] Appl. No.: 619,929

[22] Filed: Nov. 28, 1990

Related U.S. Application Data

[63] Continuation-in-part of Ser. No. 514,503, Apr. 25, 1990.

[51] Int. Cl.$^5$ ............................................... A61F 2/28
[52] U.S. Cl. .............................................. 623/16; 623/66
[58] Field of Search ................................... 623/16, 66, 18

[56] References Cited

U.S. PATENT DOCUMENTS

| | | | |
|---|---|---|---|
| 3,900,636 | 8/1975 | Curry et al. | 427/38 |
| 3,925,116 | 12/1975 | Engel | 148/143 |
| 4,465,524 | 8/1984 | Dearnaley et al. | 148/31.5 |
| 4,490,190 | 12/1984 | Speri | 148/16.6 |
| 4,568,396 | 2/1986 | Vardiman | 148/133 |
| 4,693,760 | 9/1987 | Sioshansi | 623/16 |
| 4,743,308 | 5/1988 | Sionshansi et al. | 428/217 |
| 4,743,493 | 5/1988 | Sioshansi et al. | 428/217 |

*Primary Examiner*—David Isabella
*Assistant Examiner*—Debra S. Brittingham
*Attorney, Agent, or Firm*—Morse, Altman, Dacey & Benson

[57] ABSTRACT

An improved surgical implant, formed of cobalt-chromium and its alloys in contact with a bearing surface formed by UHMWPE, and a process of its manufacture are disclosed. The improved surgical implant is designed to reduce the wear of the UHMPE component of the surgical implant, enhancing its useful life. The process essentially includes the ion implantation of the cobalt-chromium component, with a resultant increase in its microhardness and a decrease in its coefficient of friction, particularly when articulating against the UHMWPE component.

5 Claims, 6 Drawing Sheets

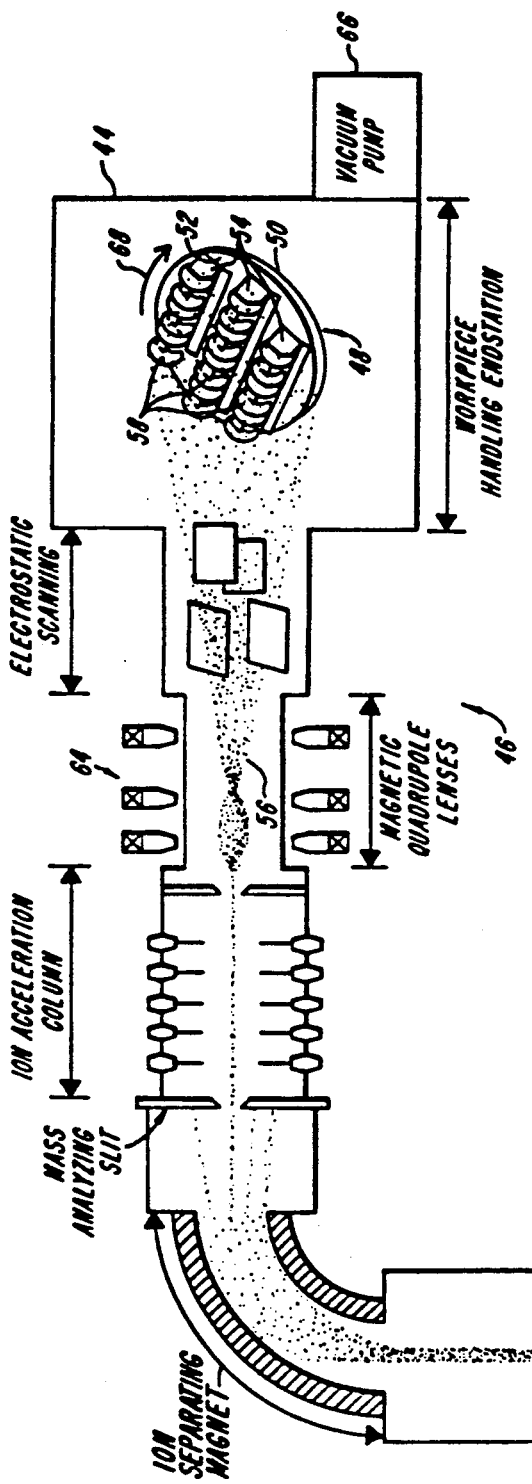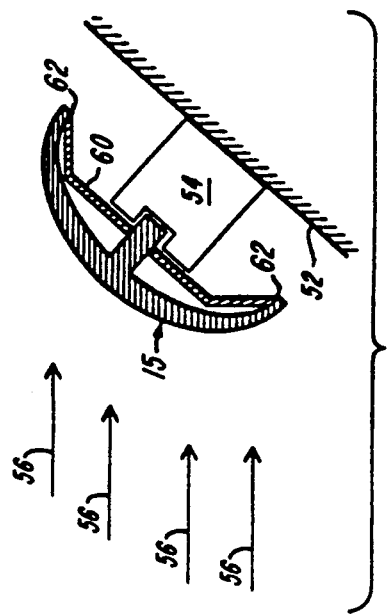
Fig. 3
Fig. 4

Coefficient of Friction against UHMWPE

| CONTROL | .138 |
|---------|------|
| IMPLANTED | .103 |

Fig. 7

Microhardness

| LOAD | 10g |
|------|-----|
| CONTROL | 886 |
| IMPLANTED | 1773 |

Fig. 8

SURGICAL IMPLANTS AND METHOD

This is a continuation-in-part application of pending application Ser. No. 07/514,503, filed Apr. 25, 1990 and assigned to a common assignee, Spire Corporation, Bedford, Mass., the disclosure of which is incorporated herein by reference.

BACKGROUND OF THE INVENTION

1. Field of the Invention

The present invention relates generally to surgical implants and, more particularly, to improved surgical implants formed of cobalt-chromium and its alloys, and a process of ion implanting the same.

2. The Prior Art

Surgical implants are widely used today in total joint replacements involving deteriorating or damaged hips, knees, shoulders, toes, fingers and elbows.

Surgical implants essentially comprise two parts: a metal part formed with an articulated surface designed to be received in and rub against a complementary load-bearing plastic surface of either an all-plastic part or a metal part with a plastic surface. The choice of metal for the metal part is either titanium and its alloys or cobalt-chromium and its alloys. The choice of plastic for the plastic part is, for the most part, ultra-high molecular weight polyethylene (UHMWPE). In use, both the metal part and its complementary plastic part experience abrasion and wear, but such abrasion and wear are more pronounced with respect to the plastic part. Until recently, the excessive wear of the plastic part has been tolerated and was considered acceptable eventually to wear away in a sacrificial manner. This was so since problems associated with the implant's attachment (or rather the lack of it) to bone to bone and with the rate of rejection of the implant by the body have been considered more significant than the wear of the plastic part. In fact to some extent, the wear representing the implant's useful life, has for the most part been designed into the implant. Recently, the problem of implant-attachment to the surrounding bone has been quite successfully addressed, inter alia, by applying porous coatings to the implant's surface. The problem of body-rejection has been countered with anti-rejection drugs and medication. These advances have caused the wear problem in the plastic component (UHMWPE) to be reassessed. Consequently, there is now a great deal of concern in the medical device industry focusing on the wear of the plastic component in an implant, since the wear has now become the determinant factor for the useful life of the implant in a patient.

In U.S. Pat. No. 4,743,493, entitled "Ion Implantation of Plastics" and assigned to said common assignee, Spire Corporation of Bedford, Mass., this wear problem was addressed with some success by ion implanting the plastic surface to a depth from about 0.1 to about 5 micrometers so as to increase its surface hardness and its resistance to chemical attack. A process for preventing surface discoloration of implants formed of titanium and its alloys, which titanium implants have been ion implanted to improve their wear performance, is disclosed in U.S. Pat. No. 4,693,760, entitled "Ion Implantation of Titanium Workpieces Without Surface Discoloration," also assigned to the said common assignee, Spire Corporation of Bedford, Mass. Implants made from cobalt-chromium and its alloys, while exhibiting good wear resistance, suffer from poor biocompatibility. A process of passivating the electro-chemically active surface of such cobalt-chromium alloys, hence inhibiting their corrosion, is disclosed in U.S. Pat. No. 4,743,308, entitled "Corrosion Inhibition of Metal Alloys," also assigned to the said common assignee, Spire Corporation of Bedford, Mass. This process essentially comprises the forming of a coating of biocompatible element from either platinum, gold or palladium on the surface of the cobalt-chromium implant, preferably by physical vapor deposition and exposing the thus coated surface to ion implantation.

The said copending application Ser. No. 07/514,503, filed Aug. 25, 1990, of which the present application is a continuation-in-part, has addressed the improving of the wear resistance of surgical implants made from titanium and its alloys by ion implantation. The present invention is intended, in contrast, to improve the wear performance of the plastic component of a surgical implant by ion implanting, not the plastic component but rather the metallic component of the implant, with the metallic part of the implant made, not from titanium and its alloys but rather from a cobalt-chromium alloy.

SUMMARY OF THE INVENTION

The present application is a continuation-in-part of pending application Ser. No. 07/514,503 filed Apr. 25, 1990 by Sioshansi et al, one of the co-inventors herein, and assigned to said common assignee, Spire Corporation of Bedford, Mass., the disclosure of which is incorporated herein by reference.

It is a principal object of the present invention to overcome the above disadvantages by providing an improved surgical implant made of cobalt-chromium and its alloys and a process of making the same.

More specifically, it is an object of the present invention to provide a surgical implant, formed of cobalt-chromium and its alloys and including a metal part formed of a cobalt-chromium alloy and a plastic part formed of UHMWPE, with the metal part of the implant being ion implanted with one of a group consisting of $N^+$, $N_2^+$, $C^+$, $Ti^+$, $Ar^+$, $B^+$, $Ne^+$, $Kr^+$, $He^+$, $P^+$ and $O^+$. The implant preferably is one of a group including prosthesis for artificial hips, knees, shoulders, wrists, elbows, fingers and toes. Preferably, the ion implantation is effected with an ion beam possessing an energy between about 20 keV and about 400 keV, a current density between about 0.1 and about 100 uA/cm$^2$, and a dose between about $1 \times 10^{16}$ and about $1 \times 10^{18}$ ions/cm$^2$.

The ion implantation is designed to create a surface region in the ion implanted cobalt-chromium surfaces that is characterized by: (1) a decrease in its coefficient of friction when rubbing against its complementary plastic part, (2) improved resistance to chemical attack and (3) a surface region with a microhardness of at least about 1200 Knoop for a 10 grams load. Preferably, the cobalt-chromium part of the surgical implant is a Co-Cr-Mo alloy, such as ASTM F-75 or F-799 alloy. Preferably, the plastic material of choice for the vast majority of total joint replacements is ultrahigh molecular weight polyethylene (UHMWPE) articulating against a mating surface formed of either a Ti-6Al-4V alloy, or a cobalt-chromium alloy. Note R. M. Rose et al., "Exploratory Investigations on the Structure Dependence of the Wear Resistance of Polyethylene," *Wear,* 77 (1982), pp. 89-104; R. M. Rose et al., "On the Pressure Dependence of the Wear of Ultrahigh Molecular Weight Polyethylene," *Wear,* 92 (1983), pp. 99-111; R.

M. Rose et al., "Radiation Sterilization and the Wear Rate of Polyethylene," *Journal of Orthopaedic Research,* 2: 393-400; and I. C. Clarke et al., "Wear of Ti-6Al-4V Implant Alloy and Ultrahigh Molecular Weight Polyethylene Combinations," *Titanium Alloys in Surgical Implants.* ASTM, STP 796 (1983), p. 136.V.

The process of forming an improved surgical implant according to the invention essentially includes forming an implant of two parts: a first metallic part formed of cobalt-chromium and its alloys and a second complementary plastic part formed of UHMWPE, exposing all aluminum fixtures and shields mounted within an implant chamber to an ion beam so as to cleanse them of surface contamination and to form a surface layer thereon having a sputtering coefficient lower than that of cobalt-chromium, creating a vacuum within the ion implantation chamber of about $3 \times 10^{-6}$ torr, introducing the first metallic part into the ion implantation chamber to be secured therein by the cleansed and surface layer coated or aluminum fixtures, and exposing the articulating surfaces of the first metallic part of the implant to a direct line of the ion beam, with the ion beam having an ion beam power density on the surface of the implant not exceeding about 100 uA/cm$^2$ at 360 kV, i.e. 36 watts/cm$^2$, the ion beam incorporating one of a group of elemental species consisting of nitrogen, carbon, titanium, argon, boron, neon, krypton, helium, phosphorus and oxygen, exposing the first metallic part of the implant to the ion beam for a period of about four to about forty hours, with an ion beam particle energy from about 20 keV to about 400 keV so as to implant a dose of about $3 \times 10^{17}$ ions/cm$^2$, and wherein the ion beam current density is between about 0.1 and about 100 uA/cm$^2$.

The ion implantation increases the microhardness of the Co—Cr—Mo alloy's surface more than two-fold and decreases its coefficient of friction when rubbing against the complementary UHMWPE part from about 0.138 to about 0.103.

Other objects of the present invention will in part be obvious and will in part appear hereinafter.

The invention accordingly comprises the surgical implant of the present disclosure, its components, parts and their interrelationships, and the method of making the same, the scope of the which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 3 is a schematic view of an ion implanter useful in carrying out the process of the invention;

FIG. 4 is a side elevation, partly in section and on an enlarged scale, of an implant exposed to the process of the invention according to FIG. 3;

FIGS. 7 and 8 are tables, indicating the coefficient of friction of an implanted vs. a non-implanted Co—Cr part rubbing against UHMWPE and, the microhardness of an implanted vs. a non-implanted Co—Cr part, respectively;

DETAILED DESCRIPTION OF PREFERRED EMBODIMENTS

In general, the present invention pertains to an improved surgical implant formed of two parts a cobalt-chromium part designed to wear against a complementary second plastic part preferably formed of ultra-high molecular weight polyethylene (UHMWPE). Cobalt-chromium and its alloys, ion-implanted according to the invention, are designed significantly to reduce the wear and abrasion of the UHMWPE part in a wide variety of orthopaedic implants.

Titanium-based alloys and cobalt-based alloys have come to be the preferred metals for use as surgical implants. In use, both the metal part and its complementary plastic part experience abrasion and wear, but such abrasion and wear are much more pronounced with respect to the plastic part. Until recently, the excessive wear of the plastic part has been tolerated and was considered acceptable. This was so since problems associated with the implant's attachment (or rather the lack of it) to bone and with the rate of rejection of the implant by the body have been considered more significant than the wear of the plastic part. Recently, the problem of implant-attachment to the surrounding bone has been quite successfully addressed, inter alia, by applying porous coatings to the implant's surface. The problem of body-rejection, on the other hand, has been countered with anti-rejection drugs and medication. These advances have caused the wear problem in the plastic component (UHMWPE) to be reassessed. There is thus a great deal of concern in the medical device industry focusing on the wear of the plastic component in an implant, since that wear has now become the determinant factor for the useful life of the implant in a patient. The present invention addresses the problem of the wear rate of the UHMWPE part in an implant by ion implanting the cobalt-chromium part of the implant constantly rubbing against the plastic part.

Figure 2:
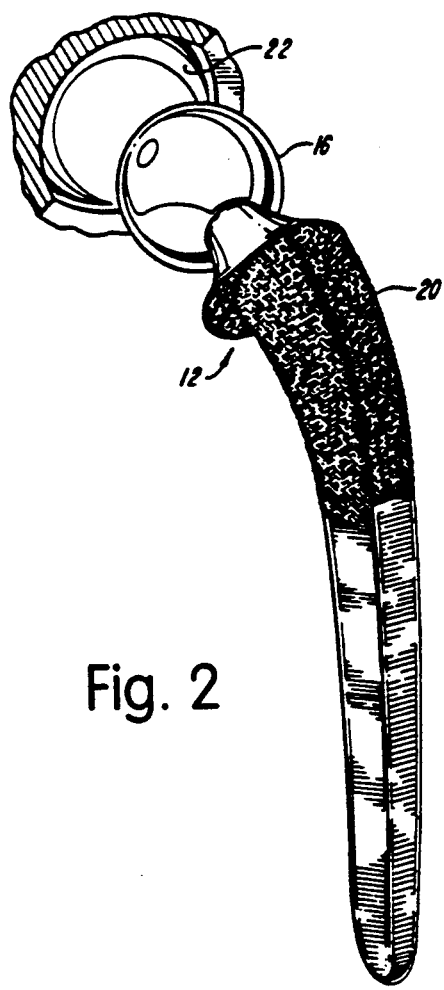
FIG. 2 is a perspective view of an artificial hip-joint prosthesis also made of two parts: a cobalt-chromium part and a complementary plastic part.
Figure 1:
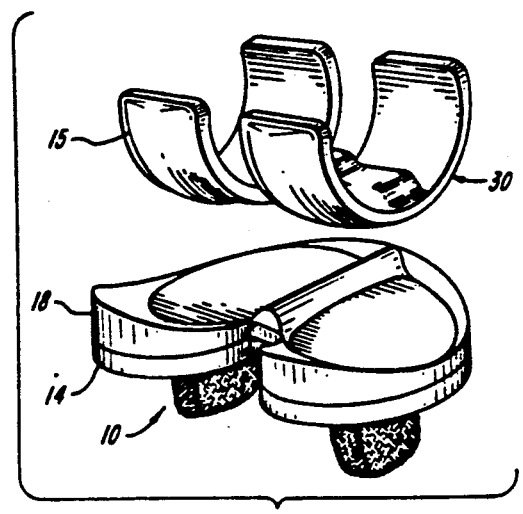
FIG. 1 is a perspective view of an artificial knee joint prosthesis made of two parts: a cobalt-chromium part and a complementary part whose load bearing surface is formed of UHMWPE.

In FIGS. 1 and 2 are illustrated artificial prosthesis for a knee joint 10 in the former and for a hip joint 12 in the latter. Each prosthesis 10 and 12 comprises at least one element formed of metal and a complementary mating element formed of plastic. The illustrated knee joint prosthesis 10 thus is formed of two metal parts 14 and 15, separated by a plastic part 18. The parts 14 and 15 preferably are formed of a cobalt-chromium alloy, such as the surgical ASTM F-75 or F-799 alloy. The plastic part 18 on the other hand is preferably formed of ultrahigh molecular weight polyethylene (UHMWPE). In like fashion, the hip joint prosthesis 12 is formed of a metal part 20 having a hemispherical ball portion 16, preferably formed of surgical ASTM F-75 alloy, and a plastic part 22, also preferably formed of UHMWPE. It is understood that the metal part 20 is placed into the femur, either by a cemented or cementless process.

During walking, the alloy ball portion 16 articulates against the UHMWPE cup part 22. In like fashion, the metal part 15 of the knee joint prosthesis 10 works against the UHMWPE part 18 during walking. The conditions of loading, sliding velocity and body chemistry that obtain in and about the respective knee and hip prosthesis 10 and 12 in the body are such as tending to produce corrosion and wear in the Co—Cr alloy and wear to a more pronounced extent in the UHMWPE component.

The ion implantation process of the invention is preferably carried out in a suitable ion implantation chamber 44 of a specially designed endstation 46 of a suitable high current ion implanter, such as a Varian-Extrion 200 kV implanter, an Eaton-Nova implanter or a like instrument. The endstation 46 is illustrated in FIG. 3.

Within the ion implantation chamber 44, a suitable fixture 48 is mounted on a base 50 designed for rotating and cooling a titanium or aluminum base plate 52. On the base plate 52 are mounted a plurality of appropriately shaped workpiece holders 54, also made of aluminum. These workpiece holders 54 are designed to hold securely a plurality of workpieces 58 and directly expose these workpieces 58 to an incoming ion beam 56. The illustrated workpieces 58 are the cobalt-chromium alloy parts 15 of the knee joint prosthesis illustrated in FIG. 1. It is to be understood that the shape of the particular workpiece holders secured to the base plate 52 will depend upon the shape of the particular workpieces being processed at that time. In FIG. 4 is illustrated one such workpiece, a cobalt-chromium alloy part 15 and secured to one of the workpiece holders 54.

As evident from viewing FIGS. 3 and 4, the fixture 48 is so designed as to expose, at one time or another, all surfaces of the workpieces directly to the ion beam 56. Any surface of the workpiece which cannot be exposed directly to the ion beam 56 must be shielded by an aluminum shield 60. It is imperative that the shield 60 fit flush with the edges of the part 15 in the back, as at 62. This flush-fitting is important to prevent the ion beam 56 from sputter depositing material around the corners of the part 15 and thus discolor the part 15 in the back.

In the practice of the process of the invention, it is important that first all fixtures 48 and shields 60 in the chamber 44 be conditioned or seasoned by being exposed to a full ion implantation dose before performing any ion implantation on the cobalt-chromium alloy parts 15 within the implantation chamber 44. Such a full ion implantation dose preferably is about $3 \times 10^{17}$ ions/cm$^2$ at the surfaces of the fixtures and shields, and extending about 100 nm below those surfaces. Such a dose preferably is effected with the ion beam 56 applied to the surfaces for a period of about three and a half hours, with an ion beam particle energy from about 10 keV to about 200 keV. The ion beam 56 preferably incorporates one of a group of elemental species, including nitrogen, oxygen, carbon, titanium, beryllium, neon, krypton, helium, phosphorus, argon and other noble gases.

The conditioning or seasoning of the surfaces of all fixtures and shields within the implantation chamber 44 achieves two important functions: first it serves to remove any surface contamination and that may be present on the surfaces of these fixtures and shields and, second it serves to form an appropriate surface layer on the fixtures and shields. The composition of the surface layer will, of course, depend which one of the elemental species, mentioned above, is incorporated in the ion beam 56. This newly formed surface layer, such as an aluminum oxide (Al$_2$O$_3$) or aluminum nitride (AlN) layer, surface layer, such as an aluminum oxide (Al$_2$O$_3$) or aluminum nitride (AlN) layer, possesses a considerably lower sputtering coefficient, i.e., between about 0.06 and 0.09 at 50 keV for N$^+$ than does pure aluminum, whose sputtering coefficient is about 0.3 for 50 keV N$^+$.

The next step of the process of the invention involves the creation of a proper vacuum environment within the implantation chamber 44. To this end, a vacuum within the implant chamber 44 must be created which is less than about $5 \times 10^{-6}$ and preferably is about $2 \times 10^{-6}$ torr, averaged during the ion implantation period of the parts 15 and 20. With the proper vacuum established within the implant chamber 44, with the aid of a suitable vacuum pump 66, a plurality of the workpieces 58 are introduced within the chamber 44. Preferably, the vacuum pump 66 should be of an oil-free type so as to avoid the possibility of introducing surface contamination onto the part to be ion implanted. The actual sequence of the two steps preferably is reversed, i.e., the workpieces 58 first are introduced into the chamber 44 and mounted therein in the fixtures 48, followed by the pump-down of the proper vacuum therein, it being of importance only that during the ion implantation step itself the proper average vacuum prevails, as above specified.

With the cobalt-chromium and its alloy workpieces 58 secured in the fixtures 48 within the chamber 44, the workpieces 58, in particular their respective articulating surfaces, are exposed to a direct line of the incoming ion beam 56. In order to achieve such a direct line, the fixture 48 is caused to rotate on its base 50 by motors not shown, as indicated by an arrow 68. Careful attention must also be paid to having the proper ion beam power density acting on the surfaces of the workpieces 58. This ion beam power density acting on the surfaces of the workpieces cannot exceed about 6.0 watt/cm$^2$ and preferably is about 1.0 watt/cm$^2$. Consequently, the peak ion beam power density of an 80 keV beam should not exceed about twelve microamperes per square centimeter.

The control of the ion beam power density can be achieved in a number of ways. Preferably, and as herein illustrated, this low power ion beam current density is effected by expanding the spot size of the incoming ion beam 56 (observe FIG. 3) by a magnetic quadrupole or an electro-static lens system 64. The surfaces of the workpieces 58, now secured in the fixture 48 within the implant chamber 44, are then exposed to the incoming ion beam 56, properly modified, if need be, by the lens system 64, for a period from about four hours to about forty hours, with a preferred ion beam particle energy from about 20 keV, to about 400 keV, so as to implant a dose of about $3 \times 10^{17}$ ions/cm$^2$ and wherein the ion beam current density is between about 0.1 and about 100 uA/cm$^2$.

Figure 5:
FIGS. 5 and 6 depict pictorially, respectively, the results of corrosion resistance testing of an implanted vs. a non-implanted Co—Cr part.
Figure 6:
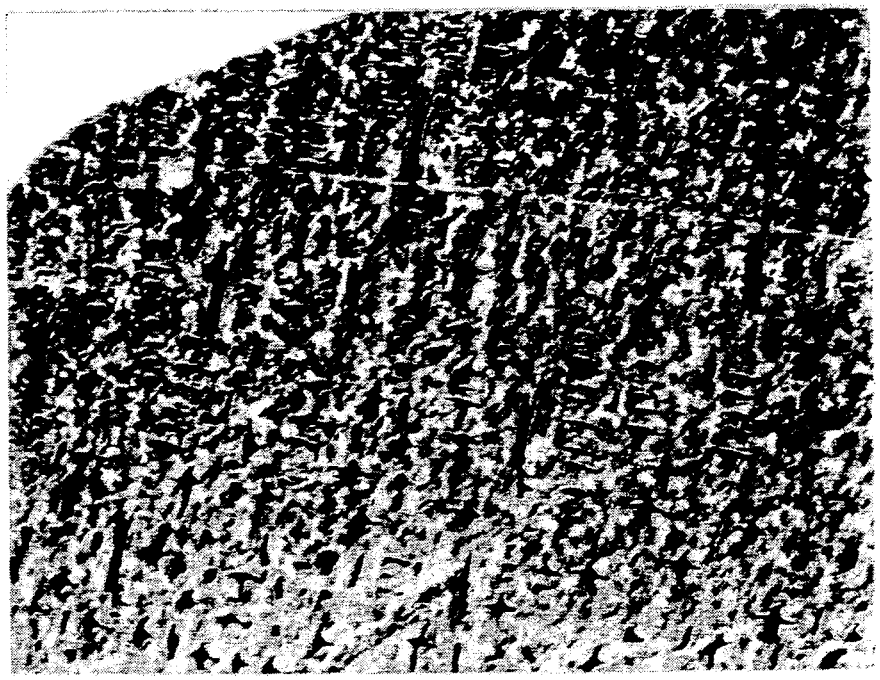

In FIGS. 5 and 6, the results of a corrosion test on cobalt-chromium alloy are depicted in pictorial form. The pictures show the surfaces of two samples, magnified fifty times, namely that of an ion-implanted sample 70 versus a non-implanted sample 72, respectively both formed of a cobalt-chromium alloy known as ASTM F-75 alloy. Sample 70 has been ion-implanted, preferably with nitrogen according to the process of the invention, while sample 72 has not been so implanted. Both samples 70 and 72 were etched by immersion in aqua regia (3 parts of HCl and 1 part Nitric, combined for 25 minutes before the test) for about 45 minutes. After drying, the surface of the implanted sample 70 indicated that it has remained virtually unaffected by the etch, revealing no evidence of corrosion. In contrast, the sample of the non-implanted sample 72 clearly shows evidence of severe pitting corrosion.

FIG. 7 and FIG. 8 indicate two important physical properties of the cobalt-chromium alloy ASTM F-75 modified by ion implantation according to the invention: namely its coefficient of friction in rubbing against a surface formed of UHMWPE and, its micorhardness expressed by the Knoop Hardness Number. (The Knoop Hardness Number serves to indicate the relative microhardness of a material, such as the Co—Cr metal alloy herein investigated, as determined by the Knoop indentation test. The higher the Knoop Number, the higher is the microhardness of the tested surface.) As is evident from the table of FIG. 7, the coefficient of friction of the implanted sample alloy rubbing against an UHMWPE surface has been reduced from about 0.138 to about 0.103. The table of FIG. 8 indicates that the microhardness of the implanted sample alloy has increased to about 1773 Knoop Number at a 10 gram load when compared to a microhardness of about 886 Knoop Number at the same 10 gram load of the non-implanted sample alloy.

FIGS. 9-12 illustrate comparisons of wear track volumes and of wear track profiles respectively of an ion implanted alloy sample versus a non-implanted sample, after correction for compression and cold flow. The test involved a pin-on-disk testing conducted in bovine blood serum in which two kinds of pins were held against a revolving disk formed of UHMWPE, first an ion-implanted Co—Cr pin working against one UHMWPE surface and, second a non-implanted Co—Cr pin working against another UHMWPE surface.

Figure 9:
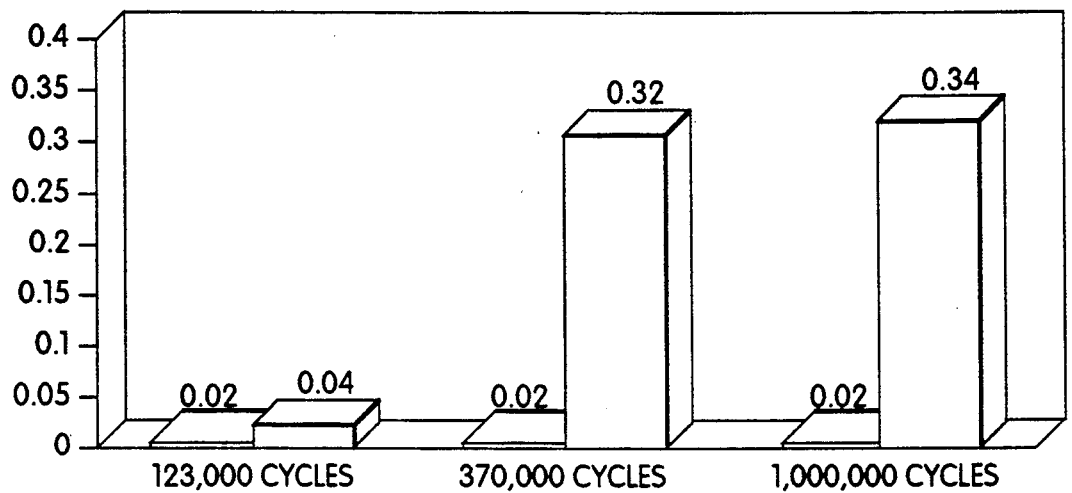
FIG. 9 is a pictorial comparison of wear track volumes from pinion disk tests on an implanted and a non-implanted Co—Cr part, per three indicated cycles.

In the track volume comparison test illustrated in FIG. 9, the relative wear at the indicated three cycles was determined using profilometry to measure the volume in $MM^3$ of the circular "track" left by revolving the pin on the disk. The sample UHMWPE disks which were wearing against the ion implanted Co—Cr pins exhibited an insignificant wear volume of about 0.02 $MM^3$ in tests conducted up to one million cycles in duration. In sharp contrast, the sample UHMWPE disks which were wearing against the non-implanted Co—Cr pins suffered considerable wear volume of about 0.04 $MM^3$ at about 123,000 cycles, about 0.32 $MM^3$ at about 370,000 cycles and about 0.34 $MM^3$ at about one million cycles. Thus, the ion implantation of the Co—Cr alloy pin demonstratably and effectively reduced the wear in the UHMWPE part by over 90% even after one million cycles.

Figure 10:
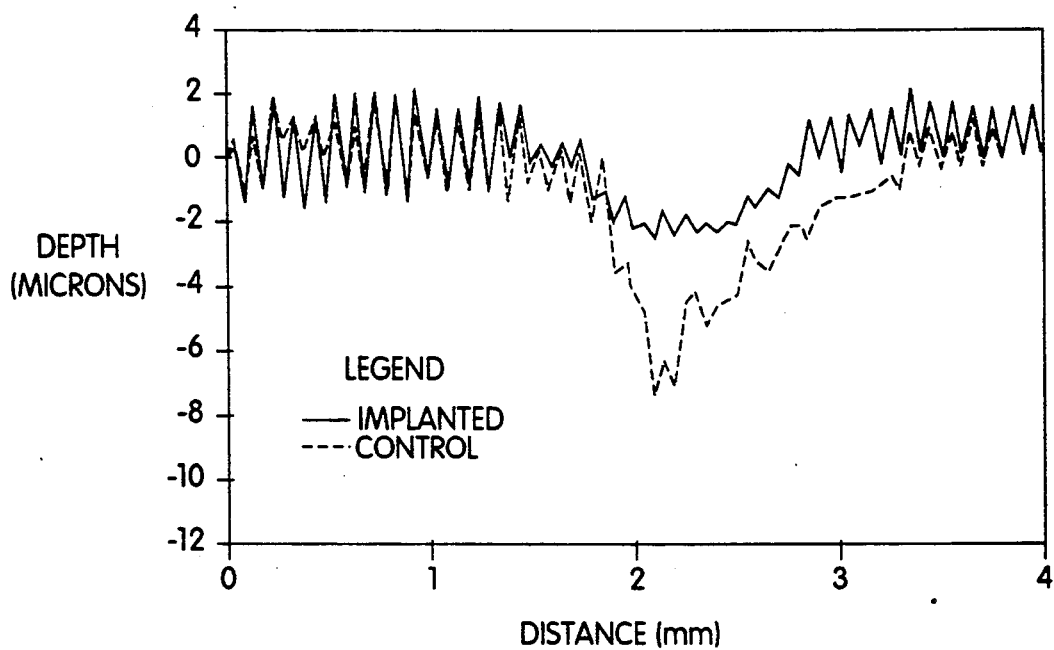
FIGS. 10, 11 and 12 depict curves representing a comparison of wear track profiles of implanted vs. non-implanted Co—Cr parts at the three cycles indicated in FIG. 9.
Figure 11:
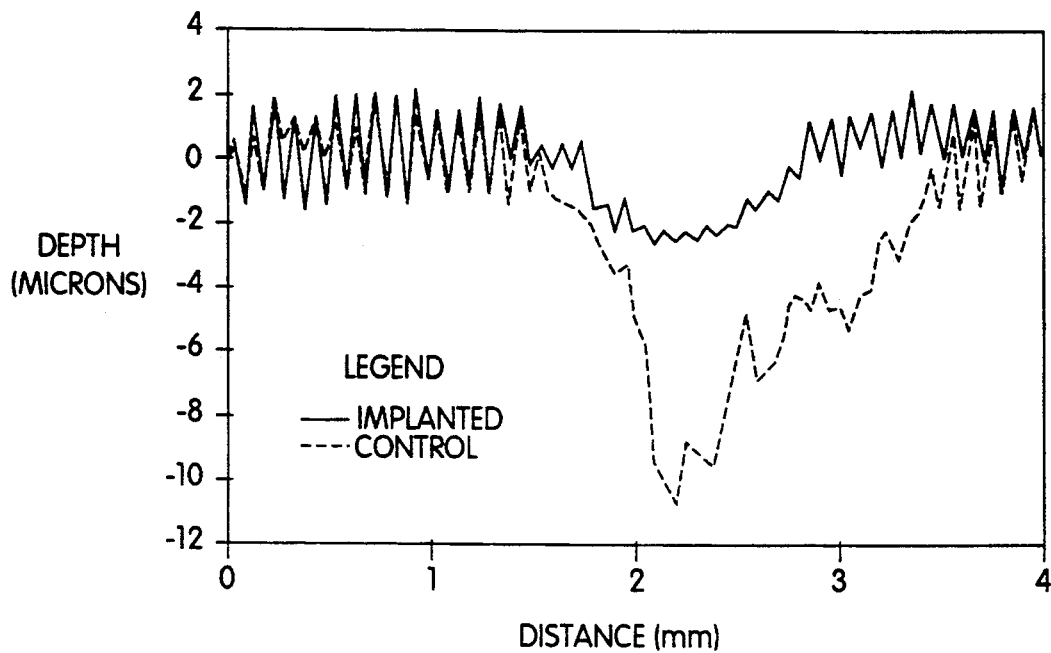
Figure 12:
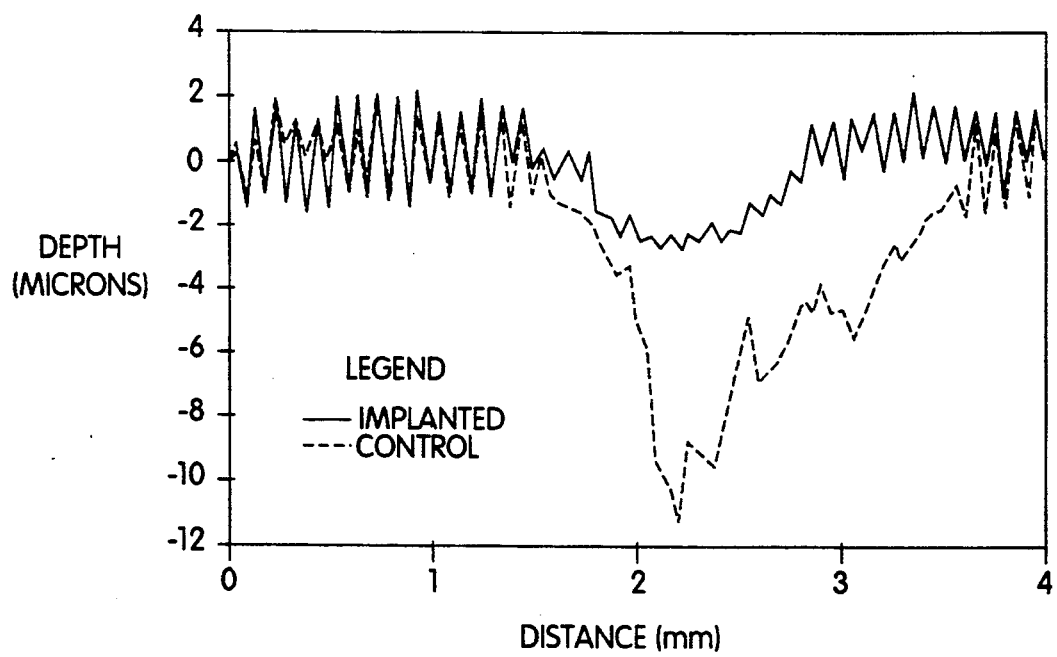

A comparison of the wear track profiles of FIGS. 10-12 at the respective 123,000 cycles, 370,000 cycles and 1,000,000 cycles bears that out, respectively plotting the depths of penetration of the UHMWPE disks by the ion implanted pins versus the control, non-implanted pins.

Thus it has been shown and described an improved orthopaedic implant made from cobalt-chromium and its alloys working against a plastic part and a process designed to improve the wear performance of the metal part against the plastic part, which product and process satisfy the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A surgical implant comprising:
   (a) an implant formed of two parts: a first part formed of metal and, a second complementary part formed of plastic;
   (b) said first metal part is formed of a cobalt-chromium alloy and said second plastic part formed of UHMWPE;
   (c) said first metal part being ion implanted with one of a group consisting of $N^+$, $N_2^+$, $C^+$, $Ti^+$, $O^+$, $P^+$, $Ne^+$, $He^+$, $Kr^+$, $Ar^+$ and $B^+$ so as to create a surface region therein characterized by an increase in its microhardness and a decrease in its coefficient of friction when rubbing against said second plastic part;
   (d) said ion implantation being effected with an ion beam power density acting on said surface region being between about 1.00 watt/$cm^2$ to about 6.0 watt/$cm^2$;
   (e) said second complementary plastic part being used as a load bearing surface supporting said surface region of said first ion implanted metallic part constantly articulating against it such that said constant articulating does not adversely affect said load bearing surface;
   (f) said ion implanted first metal part is characterized by improved surface homogeneity and resistance to chemical attack and wherein said microhardness of said metal part is at least about 1300 Knoop for a 10 gram load.

2. The surgical implant of claim 1 wherein said implant is one of a group consisting of prostheses for artificial hips, knees, shoulders, elbows, wrists, fingers and toes.

3. The surgical implant of claim 1 wherein said increase in said microhardness of said implanted metal part is at least fifty percent.

4. The surgical implant of claim 1 wherein said decrease in said coefficient of friction of said implanted metal part articulating against said UHMWPE part is from about 0.138 to about 0.103.

5. The surgical implant of claim 1 wherein said cobalt-chromium alloy is a cobalt-chromium-molybdenum metal alloy.

* * * * *